United States Patent
Yongkai et al.

(10) Patent No.: US 8,816,278 B1
(45) Date of Patent: Aug. 26, 2014

(54) IMAGING METHODS

(71) Applicant: GLOBALFOUNDRIES Singapore Pte. Ltd., Singapore (SG)

(72) Inventors: Zhou Yongkai, Singapore (SG); Zhu Jie, Singapore (SG); Du An Yan, Singapore (SG)

(73) Assignee: Globalfoundries Singapore Pte. Ltd., Singapore (SG)

( * ) Notice: Subject to any disclaimer, the term of this patent is extended or adjusted under 35 U.S.C. 154(b) by 0 days.

(21) Appl. No.: 14/019,280

(22) Filed: Sep. 5, 2013

(51) Int. Cl.
*H01J 37/26* (2006.01)
*H01J 37/305* (2006.01)
*H01L 21/32* (2006.01)

(52) U.S. Cl.
USPC ........ 250/311; 250/307; 250/306; 250/492.2; 250/492.3; 977/881; 257/E23.148; 257/E21.517

(58) Field of Classification Search
USPC ................... 250/307, 306, 311, 492.2, 492.3; 977/881; 257/E23.148, E21.517
See application file for complete search history.

(56) References Cited

U.S. PATENT DOCUMENTS

| | | | |
|---|---|---|---|
| 6,420,722 B2 * | 7/2002 | Moore et al. | 250/559.27 |
| 6,602,702 B1 * | 8/2003 | McDevitt et al. | 435/288.7 |
| 7,687,876 B2 * | 3/2010 | Kabir | 257/471 |
| 7,777,291 B2 * | 8/2010 | Kabir | 257/471 |

* cited by examiner

*Primary Examiner* — Nikita Wells
(74) *Attorney, Agent, or Firm* — Ingrassia Fisher & Lorenz, P.C.

(57) ABSTRACT

A method is provided for imaging a region of interest. The method includes defining a lamella within a microelectronic device, where the region of interest is in the lamella. The lamella has a first and second surface, and a first sacrificial layer contacts the first surface. The region of interest includes a material of interest, and an imaging technique capable of detecting the material of interest is selected. A support layer is formed on the second surface, where the support layer is transparent to the imaging technique. The first sacrificial layer is removed, and an image of the region of interest is produced.

20 Claims, 4 Drawing Sheets

IMAGING METHODS

TECHNICAL FIELD

The present embodiment generally relates to imaging methods, and more particularly relates to methods of imaging portions of microelectronic devices.

BACKGROUND

Microelectronic devices are becoming smaller and smaller as time goes on. Various electronic components, such as resistors and transistors, are manufactured and incorporated into microelectronic devices, and the shrinking size requires these electronic components to be smaller and/or more closely packed together. The small size and close packing of electronic components increases manufacturing precision required.

Some microelectronic devices include components that are less than ten nanometers (nm) thick, and millions or billions of transistors and other electronic components may be on a chip that is about the size of a fingernail. The small size and close packing of the microelectronic components requires small tolerances for each component. The small size also requires proper alignment for interconnections between different components, because chip designs specify the connections between the various microelectronic components. As the size of the microelectronic components shrink, the room for error in constructing, placing, and connecting microelectronic components also shrinks.

The manufacturing process is highly automated, and the location, timing, and use of the various manufacturing equipment is precisely controlled. Selected products are removed from the production line and inspected for quality control purposes. The selected product may be dis-assembled or cut into smaller pieces so specific components can be inspected to verify the shape, construction, alignment, positioning, etc. Many microelectronic components are too small to inspect with the naked eye, so microscopes or other techniques are used to prepare images of selected samples. The inspections allow the manufacturer to adjust and fine-tune the manufacturing equipment and processes as necessary. However, as the size of the components shrinks, the ability to inspect specific components becomes more challenging. In fact, if the sample size for inspection is too small, the sample will not retain its shape, which frustrates accurate imaging.

Accordingly, it is desirable to develop improved methods for imaging microelectronic components. In addition, it is desirable to develop new techniques and methods for isolating and imaging very small components within a microelectronic device. Furthermore, other desirable features and characteristics of the present embodiment will become apparent from the subsequent detailed description and the appended claims, taken in conjunction with the accompanying drawings and this background.

BRIEF SUMMARY

In one embodiment, a method is provided for imaging a region of interest. The method includes defining a lamella within a microelectronic device, where the region of interest is in the lamella. The lamella has a first and second surface, and a first sacrificial layer contacts the first surface. The region of interest includes a material of interest, and an imaging technique capable of detecting the material of interest is selected. A support layer is formed on the second surface, where the support layer is transparent to the imaging technique. The first sacrificial layer is removed, and an image of the region of interest is produced.

In another embodiment, the method includes defining a lamella within a microelectronic device, where a region of interest is in the lamella. The lamella has a first and second surface, and a first and second sacrificial layer contact the first and second surface, respectively. The region of interest includes a material of interest, and a transmission electron microscope imaging technique capable of detecting the material of interest is selected. The lamella and the first and second sacrificial layers are removed from the microelectronics device, and the second sacrificial layer is removed from the lamella. A support layer is formed on the second surface, where the support layer is made of a material transparent to the imaging technique. The first sacrificial layer is then removed, and an image of the region of interest is produced.

In still another embodiment, a lamella is defined within a microelectronic device, where a region of interest is in the lamella. The lamella has a first and second surface, and a sacrificial layer directly contacts the first surface. A support layer is deposited on the second surface of the lamella, and the first sacrificial layer is removed. The region of interest has a known composition, and a sample preparation technique capable of rendering that composition visible to a transmission electron microscope is used. An image of the region of interest is then produced with the transmission electron microscope.

BRIEF DESCRIPTION OF THE DRAWINGS

The present embodiment will hereinafter be described in conjunction with the following drawing figures, wherein like numerals denote like elements.

DETAILED DESCRIPTION

The following detailed description is merely exemplary in nature and is not intended to limit the application and uses of the embodiment described. Furthermore, there is no intention to be bound by any theory presented in the preceding background or the following detailed description.

Several steps are utilized to inspect small microelectronic components. A lamella or slice of the microelectronic device is defined, where the lamella includes a region of interest to be inspected. The lamella is removed from the microelectronic device with a sacrificial layer of the device on one or both sides of the lamella. The sacrificial layer(s) are carefully removed to expose the lamella for imaging and inspection. However, lamellas that are too thin may warp or bend when the sacrificial layers are removed because the lamella does not have sufficient mechanical integrity to remain flat. Imaging is compromised when the lamella warps or bends, so the resulting image may be unclear, inaccurate or incomplete. However, as the size of microelectronic components shrink, the need to image thinner and thinner lamellas increases. Therefore, a support layer can be formed on the lamella before removing the final sacrificial layer, so the support layer provides the lamella with mechanical integrity. The support layer is formed from a material that is transparent to the imaging technique, so the support layer does not interfere with the image. The lamella retains its original shape when the support layer is present, so accurate images can be produced.

Figure 1:
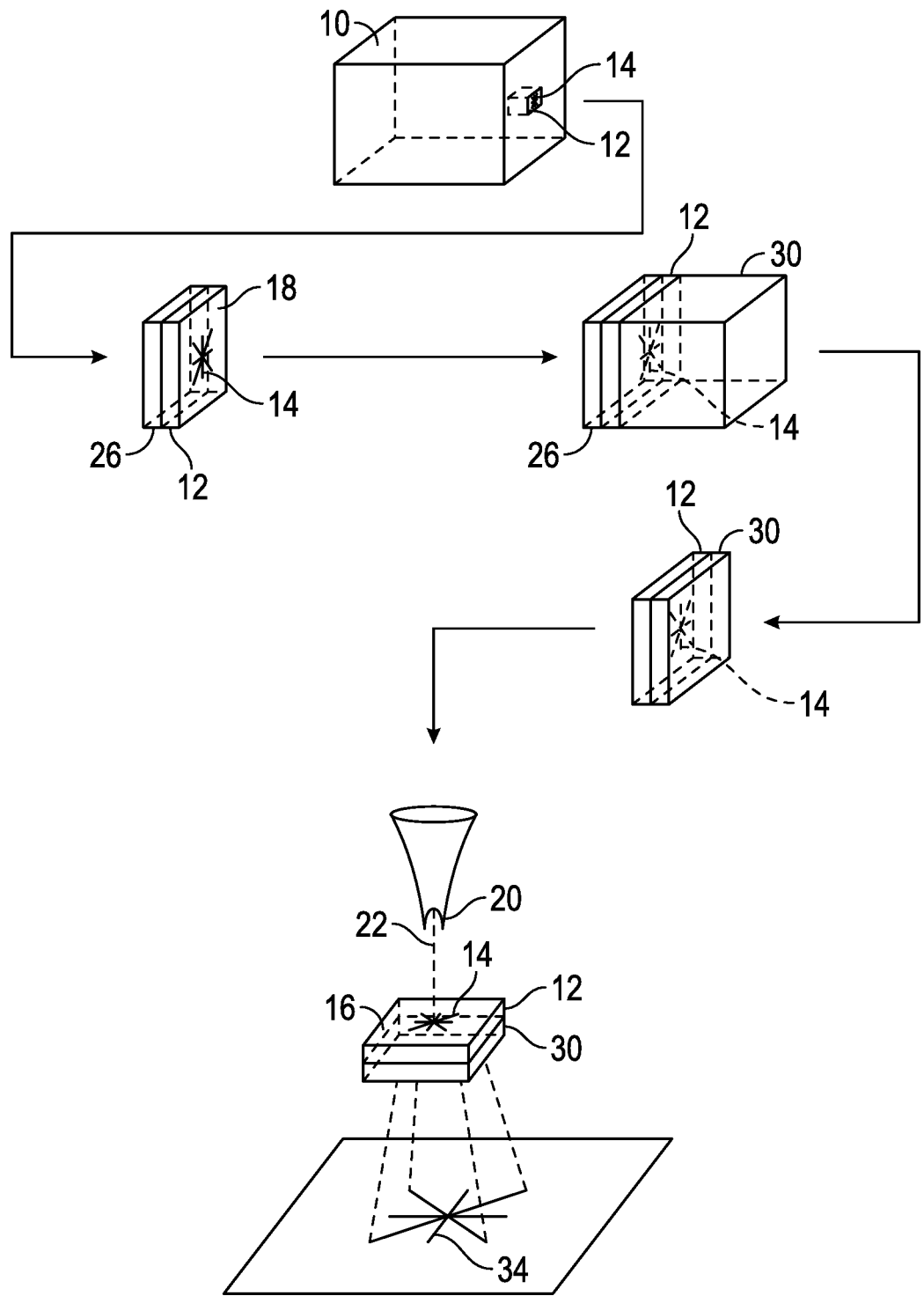
FIG. 1 illustrates one embodiment of process steps used to produce an image of a region of interest.

Reference is now made to FIG. 1. A microelectronic device 10 is provided, and a lamella 12 is defined within the microelectronic device 10. The lamella 12 is a thin sheet or slice of the microelectronic device 10, and the lamella 12 includes a region of interest 14 to be inspected. The region of interest 14 may be a contact, floating gates, a transistor or a component of a transistor, or essentially any component of the microelectronic device 10. In many embodiments, the lamella 12 is flat and relatively thin, like a piece of paper or a pane of glass, so the lamella 12 has a first surface 16 opposite a second surface 18, where the first and second surfaces 16, 18 are the largest surfaces of the lamella 12. The lamella 12 is defined to provide a view of the region of interest 14, so a slice of the microelectronic device 10 around the region of interest 14 is defined. In many embodiments, the lamella 12 is defined so the first and second surfaces 16, 18 are perpendicular to the desired view of the region of interest 14.

The region of interest 14 may be small, so the lamella 12 that contains the region of interest 14 is thin. In fact, the lamella 12 may be thin enough that it will not retain its shape when isolated. In some embodiments, a lamella 12 thinner than about 50 nanometers will not retain its shape without support from another structure, particularly for silicon based lamella 12. In some embodiments, the defined lamella 12 is no more than about 30 nanometers, but in other embodiments the lamella 12 is no more than about 20 nanometers. In yet other embodiments, the lamella 12 is no more than about 10 nanometers, and in still other embodiments it is possible to process and image a lamella 12 that is no more than about 7 nanometers thick.

The region of interest 14 may be a specific feature or component of the microelectronic device 10, or a part of a component. The region of interest 14 is a specifically selected component, so it has a known composition that includes a material of interest. The entire region of interest 14 may be formed from the material of interest, or selected portions of the region of interest 14 may be formed from the material of interest, and the material of interest 14 may vary from one inspection to the next.

Different imaging techniques are better suited for certain materials, so an imaging technique that is capable of imaging and viewing the known material of interest 14 is selected. Transmission electron microscopy (TEM) is one imaging technique that may be useful in many embodiments. TEM utilizes an electron source 20 that emits electrons 22 at the target, where the target is all or part of the region of interest 14. In TEM, the electrons 22 pass through the target and produce an image 24 on the opposite side of the target from the electron source 20. The image 24 may be displayed by a variety of methods, including projecting the electrons 22 onto a fluorescent screen, capturing the image 24 on a film negative, or using an electronic display. There are several different TEM techniques that can be selected, such as varying electron beam energies, varying electron beam diameters, parallel or convergent electron beams, diffraction pattern imaging, sample preparation methods, etc.

Figure 2:
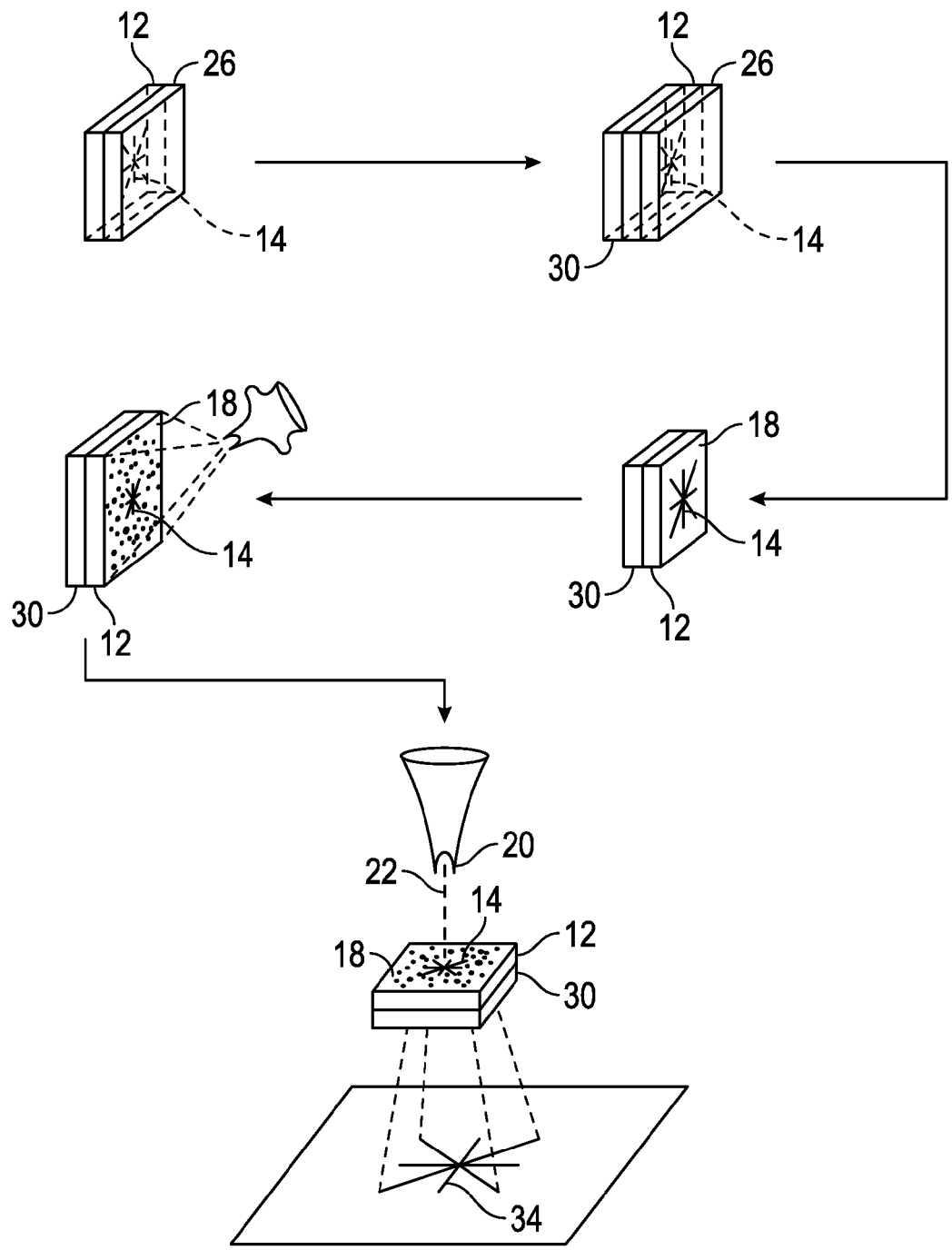
FIG. 2 illustrates another embodiment of process steps used to produce an image of a region of interest, include the use of a sample preparation technique on the lamella.

Sample preparation is one imaging technique that can impact the quality of the image 24 produced, as seen in FIG. 2 with continuing reference to FIG. 1. In some embodiments, a sample preparation technique will render the material of interest visible to the imaging technique. For example, TEM is most effective for conductive targets or samples, so non-conductive targets can be modified to increase conduction. This can include staining with various heavy metals, such as lead, uranium, or tungsten. Alternatively, the sample preparation technique can include a conductive coating, such as a gold coating of the sample. In some embodiments, the lamella 12 is cut from the microelectronic device 10 with a saw, so the orientation of the sample cut is a consideration, especially if crystallographic features are involved. Other sample preparation techniques to consider include sample dimpling prior to imaging, and different dimpling options or patterns are available. Various imaging techniques are available for TEM, and various sample preparation techniques are also available, so the user can select appropriate actions to properly view the region of interest 14.

Imaging techniques other than TEM can also be selected. These include the use of a scanning electron microscope (SEM), focused ion beam (FIB) imaging, scanning transmission electron microscope (STEM), etc. It is also possible to produce images with combined systems, such as dual beam imaging systems where an ion beam and an electron beam intersect at or near the region of interest 14. Imaging techniques that pass a photon, an electron, or another type of particle through the target are one option, but other types of imaging techniques are also possible. For example, a SEM can create an image from reflected electrons or from emission of secondary electrons, and the detectors can be on the same side of the sample as the electron source. Thinner lamellas 12 are preferred for imaging techniques that transmit photons or particles through the target, because more particles pass through a thinner lamella 12. Therefore, small components or details may not be visible if the lamella 12 is too thick.

The selected imaging technique can be a consideration in defining the lamella 12. Some imaging techniques can be more appropriate for different lamella thicknesses or orientations. Other considerations also influence the definition of the lamella 12, such as the type of component to be inspected, the purpose of the inspections, the desired point of view for the region of interest 14, crystal structure and orientation in the lamella 12, and the nature of the material of interest. The lamella 12 may be defined in different ways, such as a lamella 12 that entirely contains the region of interest 14 or a lamella 12 that displays a cross section of the region of interest 14. In many embodiments, the image 24 is produced from a perspective perpendicular to the lamella first and second surfaces 16, 18, so the lamella 12 is defined to give the desired view.

Figure 3:
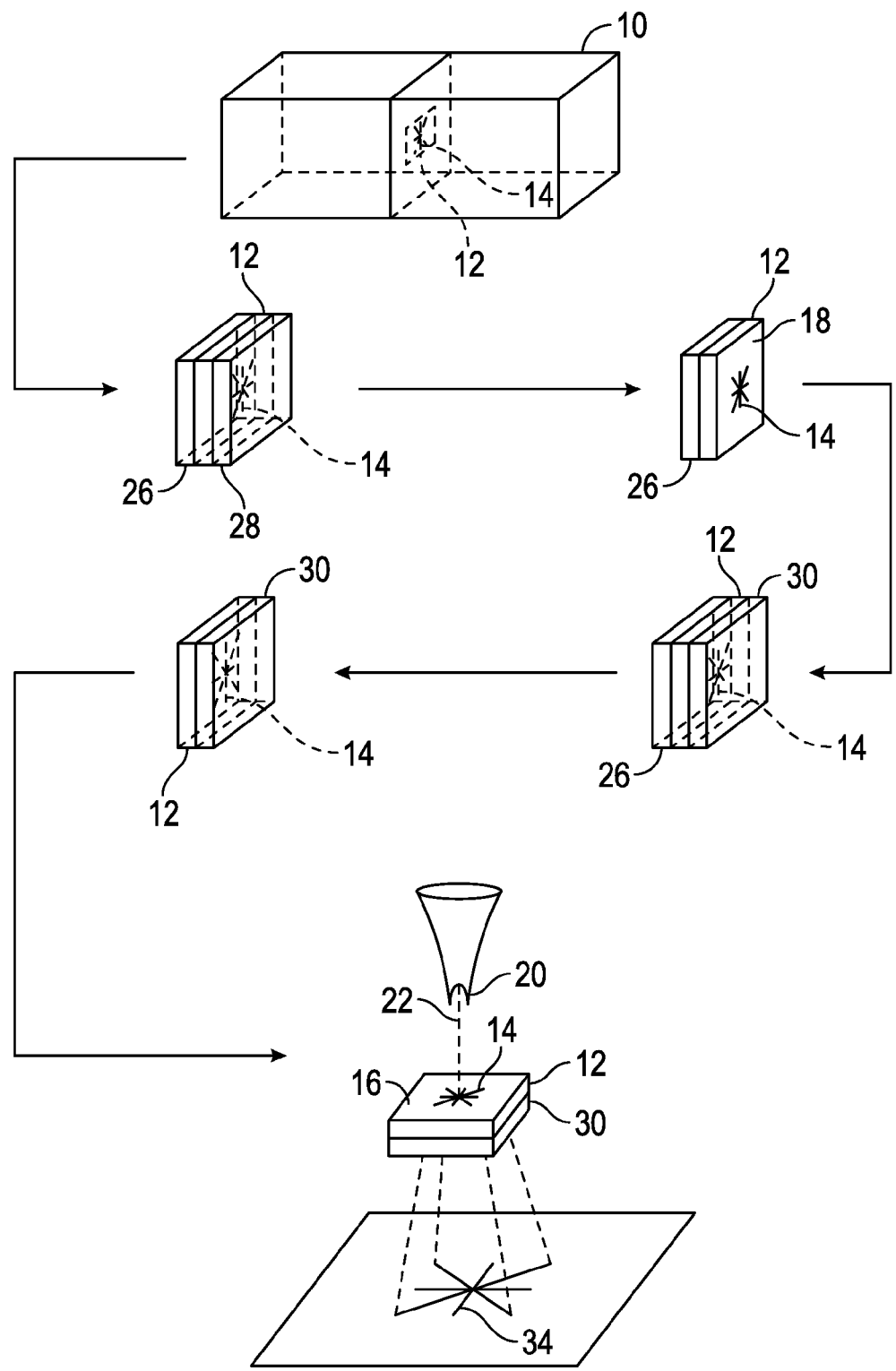
FIG. 3 illustrated another embodiment of process steps used to produce an image of the region of interest.

In some embodiments, the region of interest 14 is on an outer surface of the microelectronic device 10. The lamella 12 has a first and second surface 16, 18, so the microelectronic device 10 will only provide a sacrificial layer on one of the first and second surfaces 16, 18, and the first surface 16 is defined to be the surface with the sacrificial layer. Therefore, the lamella 12 is defined so that a first sacrificial layer 26 contacts the first surface 16 of the lamella 12. A second sacrificial layer 28 contacts the second surface 18 of the lamella 12 in some embodiments where the first and second surfaces 16, 18 are within the microelectronic device 10, as shown in FIG. 3 with continuing reference to FIG. 1. In other embodiments, a lamella 12 within the microelectronic device 10 is cut at the second surface 18, so only a first sacrificial layer 26 is present when the lamella 12 is removed from the microelectronic device 10.

The lamella 12 is removed from the microelectronic device 10, along with the first sacrificial layer 26. In some embodiments with a first and second sacrificial layer 26, 28, the second sacrificial layer 28 is also removed with the lamella 12. The lamella 12 and sacrificial layer(s) 26, 28 may be removed from the microelectronic device 10 using several different devices and methods, such as a saw, a blade, or even a milling device. The first sacrificial layer 26 should be thick enough to prevent the lamella 12 from warping or bending, which may be about 50 nanometers or more in some embodiments. However, the material and nature of the microelectronic device 10 and the lamella 12 should be considered in determining how thick the sacrificial layer(s) 26, 28 should be to prevent bending or warping. The first sacrificial layer 26 should be thick enough to prevent bending or warping of the lamella 12 regardless of whether a second sacrificial layer 28 is present or not.

Figure 4:
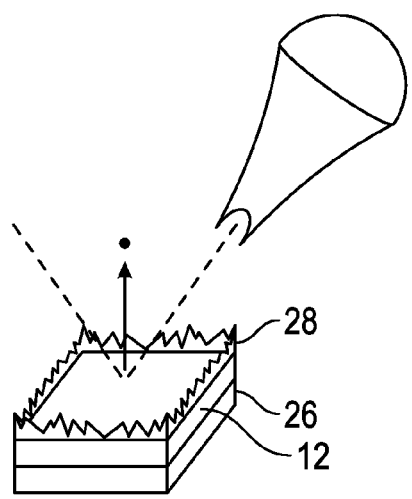
FIG. 4 is a perspective illustration depicting a focused ion beam milling a sacrificial layer from a lamella.

Once the lamella 12 is removed from the microelectronic device 10, the second surface 18 is exposed. In some embodiments, the second surface 18 is exposed on removal from the microelectronic device 10, as described above. However, in other embodiments, the second surface 18 is exposed by removing the second sacrificial layer 28 after the lamella 12 is removed from the microelectronic device 10. Milling may be used to remove the second sacrificial layer 28 from the second surface 18. In some embodiments, a focused ion beam (FIB) is used to mill the second sacrificial layer 28 from the second surface 18, as illustrated in FIG. 4. At this point, the first sacrificial layer 26 remains attached to the lamella 12 for support, so the lamella 12 retains its shape.

Figure 5:
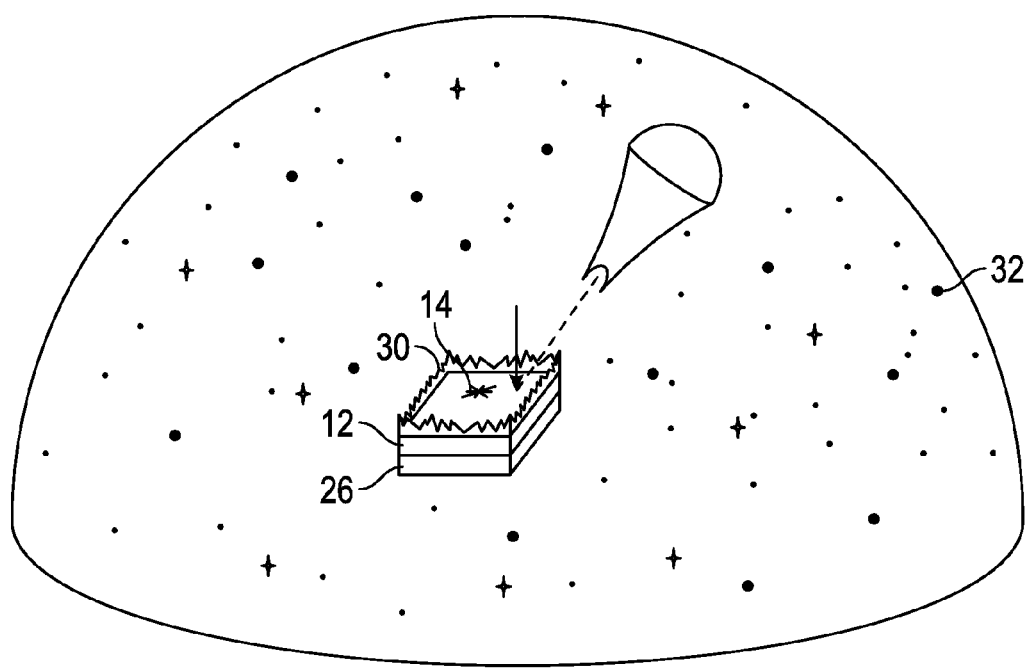
FIG. 5 is a perspective illustration depicting a focused ion beam depositing a transparent support layer on a lamella.

After the second surface 18 is exposed, a support layer 30 is formed on the second surface 18, as illustrated in FIG. 5, with continuing reference to FIGS. 1 and 3. The support layer 30 should be thick enough to support the lamella 12 and prevent it from warping or bending. In many embodiments, the support layer 30 is about 50 nanometers or more, but other thicknesses are possible. The support layer 30 should be made from a material that is ridged and strong enough to support the lamella 12 to prevent bending or warping. The support layer 30 should also be made from a material that is transparent to the imaging technique selected. Materials are generally not 100% transparent, so the term "transparent" means a material that transmits at least 80% of the imaging photons or particles at a thickness of 50 nanometers. For example, silicon oxide or silicon nitride may be transparent to many TEM imaging techniques, as are some carbon-based materials. TEM are most effective at imaging conductive materials, so various insulators may be used for the support layer 30. The imaging technique is known, so a transparent material for the support layer 30 can be selected based on the known imaging technique.

The region of interest 14 will be imaged, so a support layer 30 that does not interfere with the imaging technique is selected. For example, if the material of interest is carbon based, a silicon based support layer 30 may be selected. However, if the material of interest is silicon based, a carbon based support layer 30 may be selected. However, the material of the support layer 30 and the material of interest may be similar in some embodiments, based on the imaging technique selected. For example, if the region of interest 14 is stained or coated, the stain or coating may be applied to the first surface 16 such that the support layer 30 is not stained or coated. In other embodiments, the stain or coating is applied to the lamella 12 before the support layer 30 is formed. The stain or coating modifies the region of interest 14 such that the material of the support layer 30 can be similar or the same as the material of interest, and the support layer 30 is still transparent to the imaging technique.

An FIB may be used to form the support layer 30 on the second surface 18. The FIB can deposit a selected material on a surface, and the FIB can also be used for milling or removing material, based on different methods of operation. The FIB can use ion beam induced deposition to deposit or form a layer. Chemical vapor deposition is possible when a gas 32 is introduced over the sample and allowed to chemisorb onto the sample. The gas 32 decomposes into volatile and non-volatile components, where the non-volatile components remain on the surface and grow a new layer. An ion and/or gas 32 can be selected to deposit the support layer 30 from a variety of different materials. In other embodiments, an electron beam is used to decompose the gas 32, instead of an ion beam. Electron beam deposition expands the options for depositing the support layer 30. Machines that use either ion beams or electron beams separately or at the same time are commercially available, and these dual beam machines can be used for both depositing material and for imaging purposes. The support layer 30 can be deposited by other methods or techniques as well, such as electron beam physical vapor deposition (EBPVD).

The support layer 30 is strong and thick enough to prevent the lamella 12 from bending and warping. Therefore, the first sacrificial layer 26 may be removed after the support layer 30 is in place. The first sacrificial layer 26 may be removed by different methods, including milling with an FIB. Once the first sacrificial layer 26 is removed, the lamella 12 remains attached to the support layer 30 and therefore retains its shape. The support layer 30 is transparent to the imaging technique, so the lamella 12 can be imaged without the support layer 30 interfering with the image 24.

The selected imaging technique is then used to produce a projection or image 24 of the region of interest 14. The imaging technique may be TEM, wherein electrons are passed through the lamella 12 and region of interest 14 to produce the image 24, but other imaging techniques are possible. In some embodiments, the lamella 12 is attached to a grid, such as a copper grid, for placement and support during the imaging process. However, other techniques are available for securing samples for imaging. The image 24 can then be inspected, and appropriate quality control measures can be implemented to correct for alignment, manufacturing, or other quality issues. The manufacturing process for the microelectronic device 10 can be adjusted based on measurements and inspection of the image 24. Of course, images prepared by the method described herein can also be used for purposes other than quality control.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:
1. A method of imaging, the method comprising:
defining a lamella within a microelectronics device, wherein the lamella comprises a region of interest, a first surface, and a second surface opposite the first surface, wherein the microelectronics device comprises a first sacrificial layer contacting the first surface and a second sacrificial layer contacting the second surface, and wherein the region of interest comprises a material of interest;

selecting a transmission electron microscope imaging technique capable of detecting the material of interest;

removing the lamella, the first sacrificial layer, and the second sacrificial layer from the microelectronics device;

removing the second sacrificial layer from the second surface;

forming a support layer on the second surface after removing the second sacrificial layer from the second surface, wherein the support layer comprises a material transparent to the transmission electron microscope imaging technique;

removing the first sacrificial layer after forming the support layer; and producing an image of the region of interest with the transmission electron microscope.

2. The method of claim 1 wherein removing the second sacrificial layer from the second surface further comprises milling the second sacrificial layer from the second surface with a focused ion beam.

3. The method of claim 1 wherein forming the support layer further comprises depositing the support layer with a focused ion beam.

4. The method of claim 1 wherein removing the first sacrificial layer further comprises milling the first sacrificial layer with a focused ion beam.

5. The method of claim 1 wherein defining the lamella further comprises defining a lamella having a thickness of no more than about 30 nanometers.

6. A method of imaging, the method comprising:

defining a lamella within a microelectronic device, wherein the lamella comprises a region of interest, a first surface, and a second surface opposite the first surface, wherein the region of interest comprises a material of interest, and wherein the microelectronic device comprises a first sacrificial layer contacting the first surface;

selecting an imaging technique capable of detecting the material of interest;

forming a support layer on the second surface, wherein the support layer comprises a material transparent to the imaging technique;

removing the first sacrificial layer from the first surface after forming the support layer; and producing an image of the region of interest with the imaging technique.

7. The method of claim 6 further comprising removing the lamella and the first sacrificial layer from the microelectronic device.

8. The method of claim 7 wherein selecting an imaging technique capable of detecting the material of interest further comprises selecting a sample preparation technique capable of rendering the material of interest visible to a transmission electron microscope.

9. The method of claim 7 wherein:

defining the lamella further comprises defining the lamella wherein the microelectronic device comprises a second sacrificial layer contacting the second surface;

removing the region of interest and the first sacrificial layer further comprises removing the region of interest, the first sacrificial layer, and the second sacrificial layer; and wherein the method further comprises;

removing the second sacrificial layer from the lamella prior to depositing the support layer on the second surface of the lamella.

10. The method of claim 6 wherein defining a lamella further comprises defining a lamella having a thickness of no more than about 30 nanometers.

11. The method of claim 6 wherein removing the first sacrificial layer from the first surface further comprises milling the first sacrificial layer with a focused ion beam.

12. The method of claim 6 wherein selecting the imaging technique further comprises determining a transmission electron microscope technique capable of imaging the region of interest.

13. The method of claim 6 further comprising the step of inspecting the image of the region of interest for microelectronic device manufacturing quality control purposes.

14. A method of imaging, the method comprising:

defining a lamella within a microelectronics device, wherein the lamella comprises a region of interest, a first surface, and a second surface opposite the first surface, wherein the region of interest has a known composition, and wherein the microelectronics device comprises a first sacrificial layer directly contacting the first surface;

depositing a support layer on the lamella second surface;

removing the first sacrificial layer from the first surface of the lamella;

utilizing a sample preparation technique on the lamella that renders the known composition of the region of interest visible to a transmission electron microscope; and producing an image of the region of interest with the transmission electron microscope.

15. The method of claim 14 further comprising the step of removing the first sacrificial layer and the lamella from the microelectronic device.

16. The method of claim 15 wherein:

defining the lamella further comprises defining the lamella such that a second sacrificial layer of the microelectronics device contacts the second surface;

removing the first sacrificial layer and the lamella from the microelectronic device further comprises removing the first sacrificial layer, the second sacrificial layer, and the lamella from the microelectronic device, and wherein the method further comprises; and wherein the method further comprises;

removing the second sacrificial layer from the second surface prior to depositing the support layer on the second surface.

17. The method of claim 14 wherein depositing the support layer further comprises depositing the support layer with a focused ion beam.

18. The method of claim 14 wherein removing the first sacrificial layer further comprises milling the first sacrificial layer with a focused ion beam.

19. The method of claim 14 wherein depositing the support layer further comprises depositing a support layer that is transparent to the transmission electron microscope.

20. The method of claim 14 wherein defining the lamella further comprises defining a lamella having a thickness of no more than about 30 nanometers.

* * * * *